(12) United States Patent
Poore et al.

(10) Patent No.: US 9,339,292 B2
(45) Date of Patent: May 17, 2016

(54) MEDICAL DEVICE FOR ACCESSING SPACE ALONG AN INTERIOR SURFACE OF AN ANATOMIC LAYER

(71) Applicant: PACESETTER, INC., Sylmar, CA (US)

(72) Inventors: John W. Poore, South Pasadena, CA (US); Gene A. Bornzin, Simi Valley, CA (US); Zoltan Somogyi, Simi Valley, CA (US)

(73) Assignee: PACESETTER, INC., Sylmar, CA (US)

( * ) Notice: Subject to any disclaimer, the term of this patent is extended or adjusted under 35 U.S.C. 154(b) by 374 days.

(21) Appl. No.: 13/799,777

(22) Filed: Mar. 13, 2013

(65) Prior Publication Data

US 2014/0277056 A1    Sep. 18, 2014

(51) Int. Cl.
*A61B 17/34* (2006.01)
*A61B 17/02* (2006.01)
*A61M 25/04* (2006.01)
A61B 17/00 (2006.01)
A61B 19/00 (2006.01)

(52) U.S. Cl.
CPC .......... *A61B 17/3468* (2013.01); *A61B 17/0218* (2013.01); *A61B 17/3417* (2013.01); *A61B 17/3478* (2013.01); *A61B 17/34* (2013.01); *A61B 2017/00247* (2013.01); *A61B 2017/00349* (2013.01); *A61B 2017/0237* (2013.01); *A61B 2017/347* (2013.01); *A61B 2017/348* (2013.01); *A61B 2017/3488* (2013.01); *A61B 2019/4836* (2013.01); *A61M 25/04* (2013.01)

(58) Field of Classification Search
CPC .............. A61B 17/34; A61B 17/3417; A61B 17/3468; A61B 17/3403; A61B 17/3415; A61B 2017/00247; A61B 2017/347; A61B 2017/348; A61B 2017/3482; A61B 2017/3458; A61B 2017/3488; A61B 17/0482; A61B 17/02; A61B 17/0218; A61B 2017/0237; A61B 2017/00234; A61B 2017/00349; A61B 2017/06076; A61B 2017/3484; A61M 25/04

See application file for complete search history.

(56) References Cited

U.S. PATENT DOCUMENTS

| | | | |
|---|---|---|---|
| 5,071,428 A | 12/1991 | Chin et al. | |
| 5,171,245 A * | 12/1992 | Cezana | 606/86 R |
| 6,228,023 B1 * | 5/2001 | Zaslavsky | A61B 17/221 600/204 |
| 6,228,059 B1 * | 5/2001 | Astarita | A61B 17/3421 604/164.07 |
| 6,423,051 B1 | 7/2002 | Kaplan et al. | |
| 8,012,143 B1 | 9/2011 | Kampa et al. | |
| 2005/0070850 A1 * | 3/2005 | Albrecht | 604/167.03 |
| 2007/0135770 A1 * | 6/2007 | Hunt | A61B 1/00154 604/174 |
| 2007/0135803 A1 * | 6/2007 | Belson | 606/1 |
| 2008/0294174 A1 * | 11/2008 | Bardsley | A61B 17/3415 606/108 |
| 2012/0123461 A1 * | 5/2012 | Gillies | A61B 17/3423 606/185 |
| 2012/0136200 A1 * | 5/2012 | Miraki | 600/37 |
| 2012/0238968 A1 | 9/2012 | Toy et al. | |
| 2013/0150877 A1 * | 6/2013 | Ikeda | A61B 17/3421 606/185 |

\* cited by examiner

*Primary Examiner* — Christopher L Templeton

(57) ABSTRACT

Medical device including a lift tool having a distal end configured to removably engage an anatomic layer. The lift tool includes a shaft lumen that extends longitudinally through the lift tool and through the distal end. The shaft lumen is configured to receive an elongated insert device that is movable through the shaft lumen and through the distal end. The medical device also includes a locking mechanism that is coupled to the lift tool. The locking mechanism includes a locking member that is selectively movable with respect to the insert device between a released position and an engaged position. The locking member engages the insert device when in the engaged position to hold the insert device at a fixed position with respect to the lift tool and permits the insert device to move through the shaft lumen when in the released position.

13 Claims, 11 Drawing Sheets

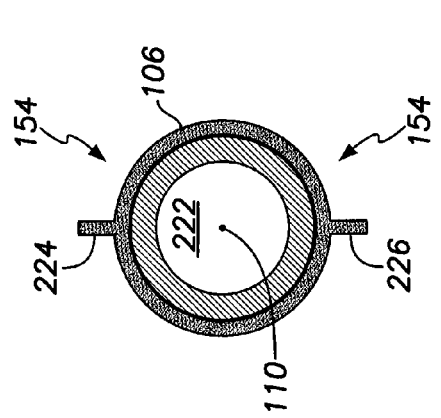
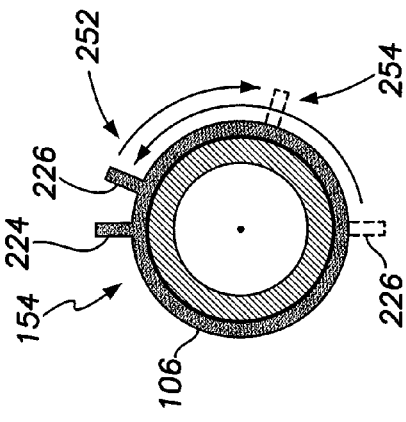
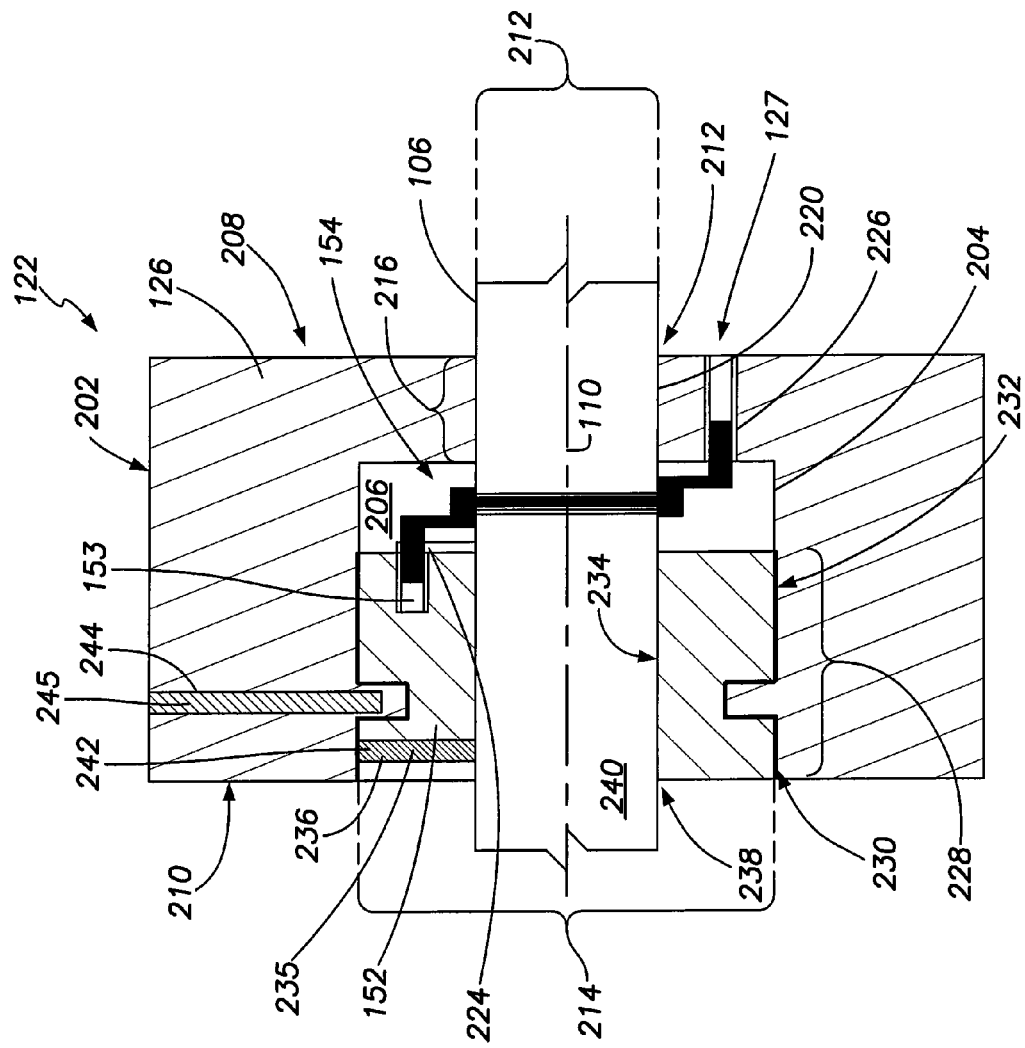

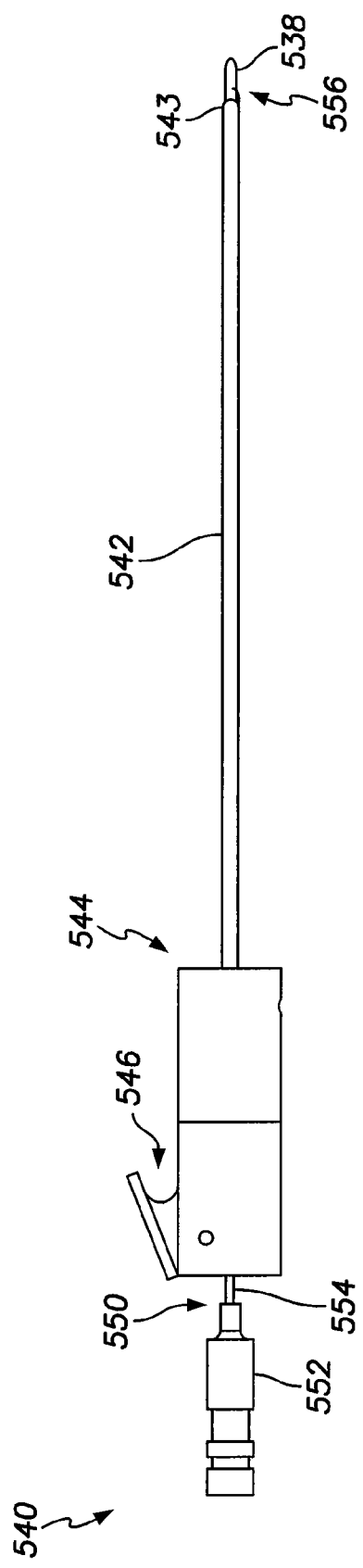
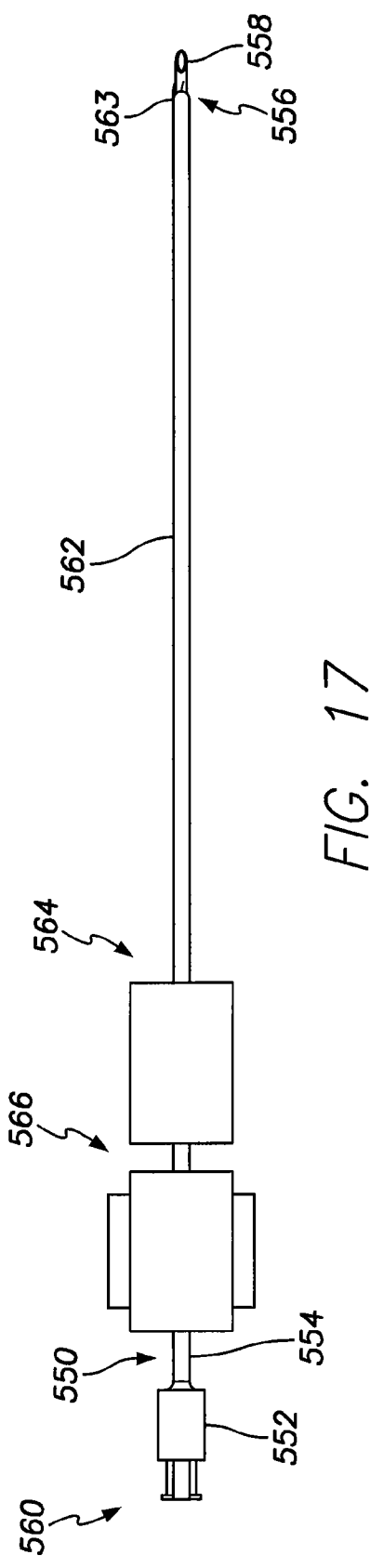

MEDICAL DEVICE FOR ACCESSING SPACE ALONG AN INTERIOR SURFACE OF AN ANATOMIC LAYER

CROSS-REFERENCE TO RELATED APPLICATION

The present application claims the benefit of U.S. Provisional Application Ser. No. 61/753,344, filed on Jan. 16, 2013, entitled "Intrapericardial Access Tool". The subject matter of this provisional application is incorporated herein by reference in its entirety.

BACKGROUND

One or more embodiments of the subject matter described herein generally relate to a device or method for accessing an interior space that extends along an anatomic layer about an organ, such as the pericardium.

The human or animal body includes different anatomic layers that separate different regions of the body. In many cases, it is desirable to insert a device through an anatomic layer without subjecting the anatomic layer or any structures behind the layer to trauma. For example, the heart is enveloped within a multi-layered sac called the pericardium. Two of the layers, the visceral pericardium and the parietal pericardium, are normally in close contact with a thin layer of pericardial fluid therebetween. This space may be referred to as the pericardial space. Access to the pericardial space may be necessary or beneficial under a variety of circumstances. For instance, with access to the pericardial space, leads for a pacemaker or defibrillator may be implanted or placed at a particular location, pericardial fluid may be drained, drugs may be delivered more directly to a portion of the heart, and a variety of other diagnostic, therapeutic and/or surgical procedures may be performed.

One method of accessing the pericardial space includes inserting a shaft through a skin incision below the xiphoid. The shaft has a distal end that may be advanced into the body until the distal end presses against the pericardium. In the known method, the distal end of the shaft includes a number of pointed tines that are configured to grab and pull the parietal pericardium. More specifically, the tines are shaped so that when the shaft is rotated, the tines pierce the parietal pericardium and become embedded therein. In this manner, the distal end of the shaft effectively grabs the parietal pericardium. The multi-tined shaft may then be pulled backward to separate the parietal and visceral pericardia and expand the size of the pericardial space. With the pericardial space expanded, a Tuohy needle may be inserted through the shaft and pierce the parietal pericardium, thereby accessing the pericardial space. Certain tools and objects (e.g., a guidewire) may then be inserted into the pericardial space through the Tuohy needle.

In another known procedure, a distal end of a percutaneous tube is positioned against the parietal pericardium in a similar manner as described above. The tube has a flow channel that extends to an opening of the distal end. However, instead of grabbing the parietal pericardium with tines, the channel may be evacuated to effectively grab a portion of the parietal pericardium. Specifically, the vacuum pulls a localized portion of the parietal pericardium into the opening to form what is called a pericardial bleb. With the bleb formed in the opening, a needle may pierce the bleb to access the pericardial space.

Although known access tools, such as the multi-tined shaft and evacuated percutaneous tube, may be suitable for gaining access to the pericardial space, the tools have certain limitations, especially after access is obtained. For example, as described above, a number of different objects may be moved through the access tools after gaining access to the pericardial space. The insertion and removal of these objects may require careful manipulation of the access tool and the objects. Frequently, the doctor may use both hands to hold the access tool, which limits the doctor's ability to insert or remove the object through the access tool. In addition, with respect to the multi-tined shaft, inadvertent rotation of the shaft may withdraw the tines from the parietal pericardium causing the shaft to release the parietal pericardium before the procedure is completed. This undesired release further complicates the procedure and may increase the risk of trauma to the patient.

Accordingly, there is a need for a medical device that enables a doctor or other qualified person to access a space located behind an anatomic layer of an individual and allow the person to insert and remove objects without the limitations of known access tools. There is also a general need for more operator-friendly medical devices that reduce the risk of trauma to the patient during a medical procedure.

BRIEF DESCRIPTION

In accordance with an embodiment, a medical device is provided that includes a lift tool having a distal end configured to removably engage an anatomic layer. The lift tool includes a shaft lumen that extends longitudinally through the lift tool and opens at the distal end. The shaft lumen is configured to receive an elongated insert device that is movable through the shaft lumen and through the distal end. The medical device also includes a locking mechanism that is coupled to the lift tool. The locking mechanism includes a locking member that is selectively movable with respect to the insert device between a released position and an engaged position. The locking member engages the insert device when in the engaged position to hold the insert device at a fixed position with respect to the lift tool. The locking member permits the insert device to move through the shaft lumen when in the released position.

In some embodiments, the locking member may be held in the engaged position. For example, the locking member may be held in the engaged position without the operator gripping or holding the locking mechanism.

In certain embodiments, the lift tool includes a plurality of tines at the distal end that engage the anatomic layer. The lift tool may have a loading end with an opening to the shaft lumen. The locking mechanism may be coupled proximate to the loading end of the lift tool.

The locking mechanism may include a shaft passage that is aligned with the shaft lumen. The locking member may be selectively movable within the shaft passage to engage the insert device. The locking member may include at least one of an elastomeric member or a contoured surface.

In some embodiments, the medical device may include the locking mechanism and a torque applicator. The torque application may include an operator-controlled movable body and a biasing member that is coupled to the movable body and secured to the lift tool. The biasing member may be capable of being flexed when the movable body is moved to change a potential energy of the biasing member. The potential energy of the biasing member biases the lift tool in a designated rotational direction.

In particular embodiments, the distal end may be sized and shaped to operatively engage a parietal pericardium during a medical procedure. The shaft lumen may be sized and shaped to receive a hollowed needle. The locking member may be configured to hold the hollowed needle in a fixed position.

In another embodiment, a medical device is provided that includes a lift tool extending along a central axis and having a distal end. The distal end is configured to grip an anatomic layer when the lift tool is rotated about the central axis in a coupling direction. The lift tool has a shaft lumen that extends longitudinally through the lift tool and opens at the distal end. The shaft lumen is configured to receive an insert device that is movable through the shaft lumen and through the distal end. The medical device also includes a torque applicator that is coupled to the lift tool. The torque applicator includes an operator-controlled movable body and a biasing member. The biasing member operatively couples the lift tool and the movable body. The biasing member is flexed when the movable body is moved relative to the lift tool to change a potential energy of the biasing member. The potential energy of the biasing member biases the lift tool in the coupling direction.

In some embodiments, the potential energy causes a tactile resistance that is detectable by an operator engaging the movable body. As such, the operator may be assured that the lift tool is still operably engaged to the anatomic layer.

The movable body may be configured to rotate about the central axis. For example, the biasing member may permit the movable body to be rotated about the central axis at least about 90° in a decoupling direction that is opposite the coupling direction while maintaining a rotational force in the coupling direction.

In certain embodiments, the biasing member includes a torsion spring having first and second ends. The first end may be secured with respect to the lift tool, and the second end may be secured to the movable body. Optionally, the torque applicator may also include a shaft holder that has a fixed position with respect to the lift tool. The shaft holder may secure a portion of the biasing member with respect to the lift tool.

Embodiments described herein may be particularly suitable for cardiac procedures, such as lead implantation or placement. As such, the medical devices may also be characterized as intrapericardial access tools or devices that are configured to expand the pericardial space. For example, the distal end of the lift tool may grab the parietal pericardium in a manner than enables the operator (e.g., doctor) to pull the parietal pericardium away from the visceral pericardium using the shaft. A needle and other objects may be inserted through the lumen of the lift tool.

In one embodiment, a method for accessing space along an interior surface of an anatomic layer is provided. The method includes coupling a distal end of a lift tool to an exterior surface of the anatomic layer. The lift tool includes a shaft lumen that extends longitudinally through the lift tool and through the distal end. The method also includes inserting an insert device through the shaft lumen. The method also includes selectively moving a locking member with respect to the insert device from a released position to an engaged position. The locking member engages the insert device when in the engaged position to hold the insert device in a fixed position with respect to the lift tool.

The distal end of the lift tool may include layer-engaging projections. In some embodiments, the coupling operation may include rotating the lift tool to embed the projections into the anatomic layer. The method may also include moving the anatomic layer to adjust the space along the interior surface of the anatomic layer.

In another embodiment, a method for accessing space along an interior surface of an anatomic layer is provided. The method includes engaging a distal end of a lift tool to an exterior surface of the anatomic layer. The lift tool includes a shaft lumen that extends longitudinally through the lift tool and through the distal end. The method also includes rotating the lift tool about a central axis of the lift tool in a coupling direction to grip the anatomic layer with the distal end. The method also includes moving an operator-controlled movable body to change a potential energy of a biasing member that is coupled to the movable body. The biasing member is secured with respect to the lift tool, wherein the potential energy of the biasing member biases the lift tool in the coupling direction so that the distal end maintains a grip on the anatomic layer. The method also includes inserting an insert device through the shaft lumen.

In some embodiments, the rotating operation and the moving operation are caused by separate rotational strokes from the operator. In other embodiments, the rotating and moving operations may be caused by the same stroke from the operator. For example, rotating the movable body may cause the lift tool to engage the anatomic layer and may also cause a change in the potential energy of the biasing member.

While multiple embodiments are disclosed, still other embodiments of the described subject matter will become apparent to those skilled in the art from the following Detailed Description, which shows and describes illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

BRIEF DESCRIPTION OF THE DRAWINGS

FIG. 4 illustrates a cross-section of a torque applicator formed in accordance with one embodiment that may be used by the medical device of FIG. 1.

FIG. 5 is an end view of a biasing member on a lift tool that may be used by the torque applicator of FIG. 4.

FIG. 6 is another end view of the biasing member on the lift tool that may be used by the torque applicator of FIG. 4.

FIG. 16 is an image of a medical device formed in accordance with one embodiment.

FIG. 17 is an image of another medical device formed in accordance with one embodiment.

DETAILED DESCRIPTION

Embodiments described herein include medical devices or access tools that enable a doctor or other qualified individual (hereinafter referred to as the operator or user) to access an anatomical space located behind an anatomic layer or wall. Although it may be suitable for the operator to directly grip the medical device, it may also be possible for the operator to control the medical device with, for example, a robotic arm. The anatomic layer may be movable (e.g., partially flexible or pliable) such that the anatomic layer may be pulled away from another structure located behind the anatomic layer. The medical device may provide a passageway that directs an insert device, such as a needle, into and through the anatomic layer.

Embodiments may include a lift tool or body that defines the passageway and receives the insert device for inserting the insert device through the anatomic layer and into the space. The lift tool may have a distal end that is configured to operatively engage or couple (e.g., grip or grab) a localized area along the anatomic layer so that localized area may be held against the distal end while the insert device is inserted. The operative engagement may be capable of holding the anatomic layer as an operator pulls the anatomic layer to enlarge the space behind the anatomic layer. In one or more embodiments, the operative engagement may be accomplished using projections or tines that are embedded into the anatomic layer. However, other embodiments may provide a suction force through the lift tool to draw a bleb into an end of the lift tool.

The medical device may also include at least one of a locking mechanism or a torque applicator. The locking mechanism may engage and hold the insert device in a fixed position relative to the locking mechanism or the lift tool. In such cases, the locking mechanism may allow the operator to use at least one of his or her hands for other purposes. The torque applicator may assist in maintaining the operative engagement between the lift tool and the anatomic layer. For example, after the lift tool is operatively engaged to the anatomic layer, the torque applicator may tolerate movement of the lift tool while still maintaining the operative engagement. In addition, the torque applicator may provide a tactile indication to the operator that confirms the anatomic layer is still operatively engaged to the lift tool.

Embodiments set forth herein may be suitable or particularly useful for accessing a space between different layers of the pericardium (e.g., the pericardial space). In certain embodiments, the anatomic layer is part of the outer layers of the heart, such as the parietal pericardium. In such cases, the medical device may be referred to as an intrapericardial access device. However, the medical devices set forth herein may also be implemented in other applications in which it is desirable to engage and hold an anatomic layer for inserting an object through the layer.

Figure 1:
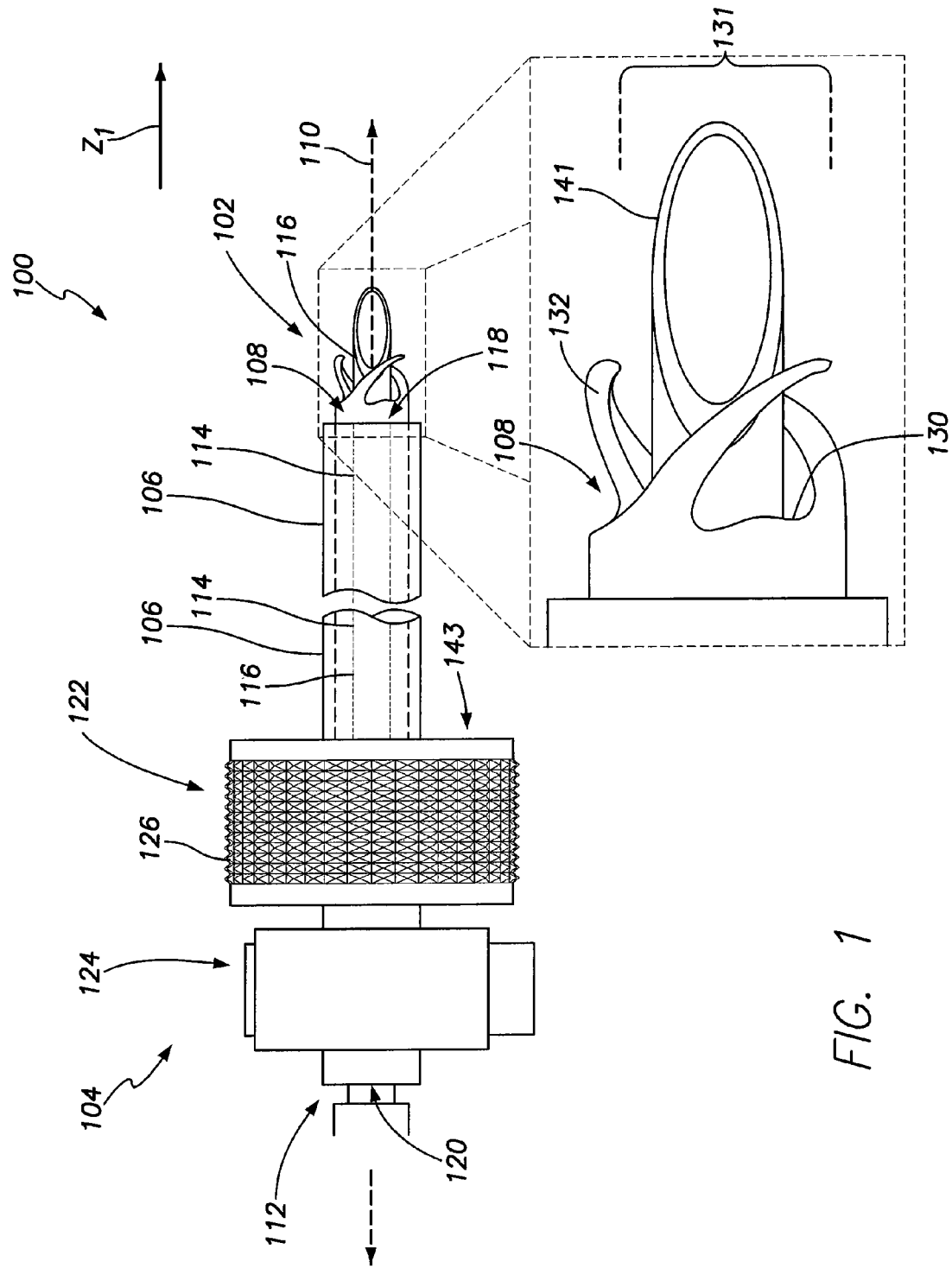
FIG. 1 is a schematic side view of a medical device formed in accordance with one embodiment.

FIG. 1 is a schematic side view of a medical device 100 formed in accordance with one embodiment. As shown, the medical device 100 extends longitudinally between an operative end portion 102 and a proximal portion 104. An intermediate portion (not shown) may join the operative end and proximal portions. The operative end portion 102 is configured to engage an anatomic layer 140 (shown in FIG. 2B) of an individual (e.g., human or non-human patient). In some cases, the operative end portion 102 is configured to be inserted into the individual. The proximal portion 104 is configured to be handled by an operator and may include mechanisms for controlling different functions and features of the medical device 100 as described herein.

The medical device 100 includes a lift tool or body 106. The lift tool 106 extends longitudinally along a central axis 110 between a distal end or tip 108 and a loading end 112. The operative end portion 102 includes the distal end 108. Optionally, the proximal portion 104 may include the loading end 112. The lift tool 106 includes a shaft lumen 114 (indicated in phantom) that is configured to receive an insert device 116. The central axis 110 may extend through the shaft lumen 114 and along a geometric center of a cross-section of the lift tool 106 that is taken transverse to the central axis 110. The shaft lumen 114 extends longitudinally through the lift tool 106 between a first opening 118 and a second opening 120. The first and second openings 118, 120 may also be referred to as distal and trailing openings. The distal and loading ends 108, 112 may include the distal and trailing openings 118, 120, respectively. The trailing opening 120 permits an insert device 116 to be loaded into the lift tool 106, and the distal opening 118 permits the insert device 116 to extend beyond or clear the distal end 108 of the lift tool 106 for insertion into the anatomic layer 140.

The shaft lumen 114 may be dimensioned to permit different types of insert devices to be inserted therein. In the illustrated embodiment, the insert device 116 is a hollowed needle (e.g., Tuohy needle), which may extend entirely through the lift tool 106 and through the distal end 108 as shown in FIG. 1. A variety of insert devices, however, may be used, provided that the objects inserts are suitably dimensioned. For example, additional insert devices may include obturators, stylets, other types of needles, tubes, guidewires, fiber-optic cable, and the like. In many instances, a first insert device may function as a tube that directs a second insert device therethrough. For example, a Tuohy needle may be inserted into and through the lift tool 106 and a guidewire may be inserted into and through the Tuohy needle.

In the illustrated embodiment, the lift tool 106 extends linearly along the central axis 110 and has a rigid or inflexible body. For example, the lift tool 106 may be a single continuous component that is formed from a rigid material, such as stainless steel. Other rigid materials that are suitable (e.g., biocompatible) for being inserted into a patient's body may be used. In other embodiments, the lift tool 106 may have a non-linear shape. Furthermore, in other embodiments, the lift tool 106 may be partially flexible along an entire length or at certain portions of the lift tool 106.

An enlarged portion of the distal end 108 is shown in FIG. 1. The distal end 108 includes an end edge 130, which may define a dimension 131 (e.g., diameter) of the distal opening 118. In some embodiments, the end edge 130 faces along the central axis 110 in an insertion direction $Z_1$ and the distal opening 118 opens in the insertion direction $Z_1$. In such embodiments, when the medical device 100 is advanced in the insertion direction $Z_1$, the lift tool 106 is aligned with (e.g., the central axis 110 may be aligned with) the insertion direction $Z_1$. However, in alternative embodiments, the distal opening 118 may open laterally with respect to the insertion direction $Z_1$. Such embodiments may be particularly applicable when the lift tool 106 (or a portion thereof) is evacuated for forming a bleb.

In the illustrated embodiment, the distal end 108 includes pointed layer-engaging projections (e.g., tines) 132. The projections 132 are shaped to pierce through the anatomic layer 140 when the distal end 108 is moved into the anatomic layer 140 with sufficient force. As shown, the projections 132 may be curved or partially helical, although other shapes may be used. When the lift tool 106 is moved to engage the anatomic layer 140, the lift tool 106 may be rotated about the central axis 110 in a designated manner. In the illustrated embodiment, the projections 132 are formed from the same material as the lift tool 106. As such, the projections 132 may also be formed from a rigid material, such as stainless steel. In other embodiments, the projections 132 may be more flexible or movable.

The medical device 100 may also include a torque applicator 122 and an operator-controlled locking mechanism 124 that are coupled to the lift tool 106. In FIG. 1, the torque applicator 122 and the locking mechanism 124 are separate bodies with different axial locations along the central axis 110. However, in other embodiments that include each of the torque applicator 122 and the locking mechanism 124, the structures and functions of the torque applicator 122 and the locking mechanism 124 may be integrated into a single body.

As described herein, the torque applicator 122 may apply a rotational force RF (shown in FIG. 3) to the lift tool 106 that facilitates maintaining an operative engagement between the distal end 108 and the anatomic layer 140. In some embodiments, the rotational force RF may also facilitate with the initial insertion of the projections 132 into the anatomic layer 140. The torque applicator 122 may be tolerant or yielding such that the torque applicator 122 is permitted to rotate the lift tool 106 in a direction that is opposite of the rotational force RF without the distal end 108 and the anatomic layer 140 becoming disengaged. The torque applicator 122 may also provide a tactile indication to the operator that confirms the distal end 108 and the anatomic layer 140 are still engaged. As shown, the torque applicator 122 includes an operator-controlled movable body 126 that is configured to be engaged (e.g., gripped and moved) by the operator.

The locking mechanism 124 is configured to be actuated by the operator to selectively lock the insert device 116 in a designated position. The locking mechanism 124 may be adjustable or movable between a released position and an engaged position. In the engaged position, the locking mechanism 124 may hold the insert device 116 at a designated axial location with respect to the central axis 110 or with respect to the lift tool 106. Optionally, the locking mechanism 124 may also be configured to hold the insert device 116 in a designated rotational orientation. For example, the insert device 116 may be rotated and then locked in a fixed position such that a beveled end 141 of the insert device 116 faces in a designated radial direction. In FIG. 1, the beveled end 141 faces out of the page.

An intermediate portion of the lift tool 106 has been removed in FIG. 1 for illustrative purposes. Nonetheless, the lift tool 106 and the medical device 100 may have a variety of lengths. For example, the lift tool 106, measured from a leading face 143 of the torque applicator 122 to the distal end 108, may have a length that is between about 8 centimeters (cm) to about 40 cm or, more specifically, about 15 cm to about 30 cm. However, the above dimensions are just examples and the medical device 100 and the lift tool 106 may have different configurations.

Figure 2A:
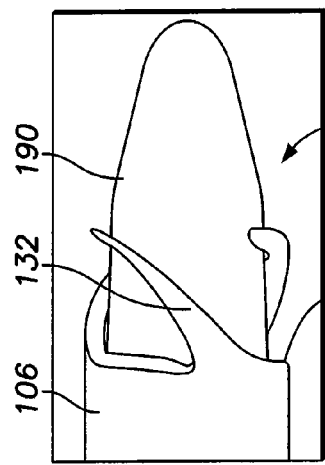
FIG. 2A is a side view of a distal end of the medical device of FIG. 1 in accordance with one embodiment prior to insertion through an incision.
Figure 3:
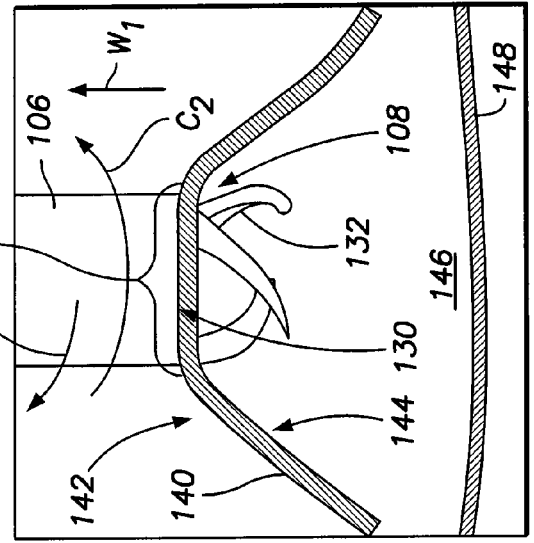
FIG. 3 is a side view of the distal end of the medical device of FIG. 1 after engaging and pulling the anatomic layer.
Figure 2B:
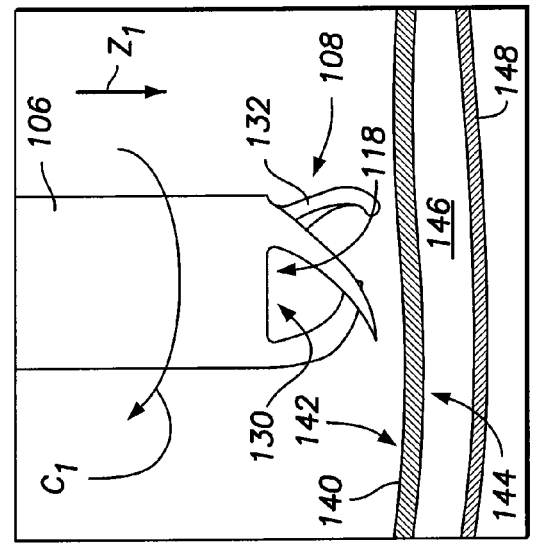
FIG. 2B is a side view of the distal end of the medical device of FIG. 1 prior to engaging an anatomic layer.

FIGS. 2A, 2B, and 3 illustrate side views of the distal end 108 of the medical device 100 (FIG. 1). It should be noted that FIGS. 2A, 2B, and 3 are used only for illustration and that the relative dimensions shown in FIGS. 2A, 2B, and 3 are not necessarily accurate. In FIG. 2A, the distal end 108 is configured to be inserted into an individual (e.g., patient). During a procedure in which the lift tool 106 of the medical device 100 is inserted into the patient, an incision (not shown) may be first made at a designated area of the patient (e.g., along the skin). Before the lift tool 106 is inserted through the incision, an obturator 190 may be advanced into the shaft lumen 114 (FIG. 1) and positioned so that the obturator 190 extends beyond the end edge 130 and beyond the projections 132 of the lift tool 106 as shown in FIG. 2A. In the illustrated embodiment, the obturator 190 is dimensioned to fill the shaft lumen 114 at the distal end 108. When the distal end 108 is inserted into the incision, the obturator 190 may block or obstruct flow of material into the shaft lumen 114. In addition, the obturator 190 may reduce the likelihood that the projections 132 snag tissue or other material in the body as the lift tool 106 is inserted.

In FIG. 2B, the distal end 108 of the lift tool 106 is positioned proximate to the anatomic layer 140. The anatomic layer 140 has first and second surfaces 142, 144 with a thickness of the anatomic layer 140 extending therebetween. As shown, the second surface 144 extends along and defines an anatomical space 146. In some cases, another anatomic layer 148 may be positioned adjacent to the anatomic layer 140 with the anatomical space 146 located therebetween. In particular embodiments, the anatomic layer 140 is the parietal pericardium, the anatomic layer 148 is the visceral pericardium, and the anatomical space 146 is the pericardial space. However, as noted herein, embodiments may be used with other anatomic layers.

During the gripping operation, the distal end 108 may be pressed against (e.g., directly engage) the first surface 142 of the anatomic layer 140. For example, as the distal end 108 is inserted through an incision (not shown) and into the body, the operator may sense or detect (e.g., based on tactile feel) that the distal end 108 is against the anatomic layer 140. With respect to intrapericardial access devices, the operator may sense palpitations or contractions of the heart. While pressed against the anatomic layer 140, the lift tool 106 may be rotated in a coupling direction $C_1$, which in FIG. 2B is clockwise from the viewpoint of the operator looking down the lift tool 106 toward the anatomic layer 140. As the lift tool 106 is rotated in the coupling direction $C_1$, the projections 132 may pierce the anatomic layer 140. In some cases, the projections 132 may pierce or partially pierce the anatomic layer 140 prior to rotation.

With the anatomic layer 140 initially penetrated, continued rotation of the lift tool 106 may drive the projections 132 deeper into the anatomic layer 140 and bring the end edge 130 and the anatomic layer 140 close to each other as shown in FIG. 3. More specifically, the shape of the projections 132, the rotation of the lift tool 106 in the coupling direction, and the pliable nature of the anatomic layer 140, may cause the anatomic layer 140 to be pulled toward the end edge 130 and/or cause the lift tool 106 to be pulled toward the anatomic layer 140. In the illustrated embodiment, the projections 132 may clear the thickness of the anatomic layer 140 and extend beyond the second surface 144. However, in other embodiments, the projections 132 may not clear the second surface 144.

With the anatomic layer 140 and the distal end 108 operatively engaged, the operator is permitted to move the lift tool 106 in a withdrawal direction $W_1$ (FIG. 3) that is opposite the insertion direction $Z_1$ (FIG. 2B). As such, the anatomical space 146 may be enlarged or expanded. In some embodiments, the distal end 108 may be configured such that a localized portion 150 of the anatomic layer 140 spans across the distal opening 118 (FIG. 2B) and is held against the end edge 130. The localized portion 150 may be held is a substantially fixed position with respect to the end edge 130 as the insert device 116 (FIG. 1) is inserted through the localized portion 150.

With respect to FIG. 3, when the distal end 108 is operatively engaged to the anatomic layer 140 as shown and the lift tool 106 is rotationally steady (e.g., is not being actively rotated), the distal end 108 remains engaged to the end edge 130 due to the shape of the projections 132. However, rotating the lift tool 106 in a decoupling direction $C_2$ (e.g., counter-clockwise) that is opposite the coupling direction $C_1$ would cause the anatomic layer 140 to slide along the projections 132. The end edge 130 and the anatomic layer 140 may then separate and, in some cases, the anatomic layer 140 may be released from the projections 132. As such, in some embodiments, it may be desirable to maintain at least some rotational force RF in the coupling direction $C_1$. The rotational force RF may maintain tension that resists rotational movement of the lift tool 106 in the decoupling direction $C_2$ and/or resists movement of the anatomic layer 140 away from the end edge 130.

FIG. 4 shows a cross-section of the torque applicator 122 in accordance with one embodiment. The torque applicator 122 may include the operator-controlled movable body 126, a shaft or tool holder 152, and a biasing member 154. The torque applicator 122 is configured to apply the rotational force RF (FIG. 3) to the lift tool 106 to facilitate maintaining the operative engagement with the anatomic layer 140 (FIG. 2B). In some embodiments, the torque applicator 122 may also be used to initially grab or grip the anatomic layer 140. for example, a single common stroke (e.g., rotation of the movable body) may cause the lift tool 106 to engage the anatomic layer 140 and also cause the lift tool 106 to provide the rotation force RF. It is noted, however, that the embodiment shown in FIG. 4 is just one example of a torque applicator that can be used with the medical devices described herein and others can be used.

As shown, the movable body 126 has an exterior surface 202 and an interior surface 204. The exterior surface 202 is configured to be engaged (e.g., gripped) by the operator. As such, the exterior surface 202 may be shaped to facilitate gripping by the operator. For example, the exterior surface 202 may include knurling or threads. The exterior surface 202 includes end portions 208, 210 that face in opposite directions along the central axis 110. In the illustrated embodiment, the end portion 208 faces toward the distal end 108 (FIG. 1) of the lift tool 106. In other embodiments, however, the end portion 210 may face toward the distal end 108. As shown, the end portion 208 includes a shaft opening 212 and the end portion 210 includes a body opening 214. In the embodiment of FIG. 4, the shaft and body openings 212, 214 are sized and shaped to receive, at the very least, the lift tool 106. The body opening 214 may also be dimensioned to receive the shaft holder 152.

The interior surface 204 may define a shaft-engaging portion 216 that engages the lift tool 106. For example, the shaft-engaging portion 216 may extend circumferentially around the lift tool 106 with a slidable interface 220 located therebetween. The interior surface 204 also defines a body cavity 206 that opens to and extends between the shaft and body openings 212, 214. In addition to the lift tool 106, the body cavity 206 may be sized and shaped to receive the shaft holder 152 and the biasing member 154.

The biasing member 154 defines a shaft-receiving opening 222 (shown in FIGS. 5 and 6) and includes member ends 224, 226 that are configured to engage the shaft holder 152 and the movable body 126, respectively. For example, the shaft holder 152 and the movable body 126 may have cavities 153, 127, respectively, that receive and engage the member ends 224, 226, respectively. The member ends 224, 226 may be engaged to the respective cavities 153, 127 through, for example, an interference fit and/or depositing an adhesive in the cavities 153, 127. The shaft-receiving opening 222 is dimensioned to receive the lift tool 106. In the illustrated embodiment, the biasing member 154 is a torsion spring, but other biasing members capable of functioning as described herein may be used.

The interior surface 204 of the movable body 126 includes a holder-engaging portion 228 and forms a slidable interface 230 with an outer surface 232 of the shaft holder 152. In the illustrated embodiment, the outer surface 232 faces radially away from the central axis 110 and the holder-engaging portion 228 of the interior surface 204 faces radially-inward toward the central axis 110. As shown, the shaft holder 152 may include an open-sided channel or groove 242 that opens to the interface 230 and the movable body 126.

When the medical device 100 (FIG. 1) is assembled, the distal end 108 or the loading end 112 (FIG. 1) of the lift tool 106 may be inserted through the body cavity 206 of the shaft holder 152 and the shaft-receiving opening 222 of the biasing member 154. The biasing member 154 may be secured to the shaft holder 152 by inserting the member end 224 into the cavity 153 and forming, for example, an interference fit.

The shaft holder 152 may also be affixed to the lift tool 106. For example, the shaft holder 152 may be secured to the lift tool 106 in a fixed position so that the lift tool 106 and the shaft holder 152 move with each other when the shaft holder 152 is moved. The shaft holder 152 may be affixed to the lift tool 106 in various manners. For example, the shaft holder 152 may include a thru-hole 236 that extends from the outer surface 232 of the shaft holder 152 to an inner surface 234 of the shaft holder 152. The inner surface 234 faces radially-inward and may define a shaft passage 238 of the shaft holder 152. The shaft passage 238 is dimensioned to receive the lift tool 106. In some embodiments, a fastener 235 (e.g., plug, set screw, and the like) may be inserted into the thru-hole 236 and directly engage an outer surface 240 of the lift tool 106 thereby affixing the lift tool 106 and the shaft holder 152 to each other.

Alternatively or in addition to, an adhesive may be placed along the inner surface 234 or the outer surface 240 of the lift tool 106 to affix the lift tool 106 and the shaft holder 152 to each other. As another example, the lift tool 106 and the shaft holder 152 may include complementary projections and recesses to form a snap-fit engagement. Furthermore, a clamp ring may surround the shaft holder 152 with the lift tool 106 positioned in the shaft passage 238 and the clamp ring may be clamped using, for example, a screw to increase the frictional engagement between the shaft holder 152 and the lift tool 106. In another embodiment, the shaft holder 152 and the lift tool 106 may be integrally formed through, for example, a common molding process. Such a shaft holder may include the member cavity 153 and/or the channel 242.

After the shaft holder 152, the biasing member 154, and the lift tool 106 are assembled together, the lift tool 106 may then be inserted through the body and shaft openings 214, 212 and the body cavity 206 of the movable body 126. The movable body 126 may be positioned to surround the shaft holder 152 and the biasing member 154.

In other embodiments, the movable body 126, the shaft holder 152, and the biasing member 154 may be pre-assembled as shown in FIG. 4 and then the lift tool 106 may be inserted therethrough. The shaft holder 152 may then be affixed to the lift tool 106 as described above or in another manner.

In the illustrated embodiment, when the medical device 100 is fully assembled, the movable body 126 is capable of being rotated around the shaft holder 152 or, more specifically, around the lift tool 106 and the central axis 110. In some embodiments, the movable body 126 may include a thru-hole 244 for receiving a fastener 245 (e.g., set screw, plug, and the like) that extends through the thru-hole 244 and into the channel 242. The fastener 245 may be configured to prevent the movable body 126 and the shaft holder 152 from moving relative to each other along the central axis 110.

In some embodiments, the fastener 245 may also limit an amount of rotation of the movable body 126. For instance, the channel 242 may not extend entirely around a circumference of the shaft holder 152. By way of a specific example, the channel 242 may only extend between about 270° and 180° about the central axis 110. In such cases, when the movable body 126 is rotated, the fastener 245 may engage, for example, a surface of the shaft holder 152 thereby stopping rotation of the movable body 126.

FIGS. 5 and 6 illustrate isolated end views of the biasing member 154 and the lift tool 106. In particular, FIGS. 5 and 6 illustrate views looking down the lift tool 106 from the distal end 108 (FIG. 1) toward the biasing member 154. The member ends 224, 226 are shown and are in the 12 o'clock and 6 o'clock positions, respectively.

For some of the embodiments set forth herein, the biasing member is configured to be moved or adjusted between different positions or configurations to change a potential energy of the biasing member. The biasing member 154 has a first condition in FIG. 5 and a second condition in FIG. 6. For some embodiments, the first condition may be a relaxed condition of the biasing member 154 and the second condition may be a biased condition in which the biasing member exerts a rotational force to return the biasing member to the first condition. In other embodiments, the biasing member 154 may be pre-loaded such that each of the first and second conditions is a biased condition, but the second condition is more biased such that the biasing member 154 exerts a greater rotational force in the second condition than in the first condition.

With respect to the illustrated embodiment, when the movable body 126 (FIG. 1) is rotated about the lift tool 106 as described with respect to FIG. 4, a potential energy of the biasing member 154 is changed. More specifically, when the movable body 126 is rotated in the coupling direction $C_1$ (FIG. 2B), the member end 226 is moved from a first radial position 250 to a second radial position 252. The biasing member 154 is configured such that the change in radial positions of the biasing member 154 increases the potential energy of the biasing member 154.

The potential energy of the biasing member 154 may correspond or correlate to the rotational force RF (FIG. 3). More specifically, in the illustrated embodiment, the biasing member 154 is secured to the shaft holder 152 due to the coupling of the member end 224 and the cavity 153 (FIG. 4). The member end 224 has a fixed relationship with respect to the lift tool 106, and the member end 226 has a fixed relationship with respect to the movable body 126. As such, the biasing member 154 is secured to the lift tool 106 and to the movable body 126. When the distal end 108 is operatively engaged to the anatomic layer 140 (FIG. 2B) and the movable body 126 is rotated in the coupling direction $C_1$ (FIG. 2B), the member end 226 rotates with the movable body 126 about the central axis 110. However, the member end 224 is secured to the shaft holder 152, which is affixed to the lift tool 106. The lift tool 106 is operatively engaged to the anatomic layer 140 such that the lift tool 106 is prevented from rotating. As such, the member end 224 is unable to rotate about the central axis 110.

Accordingly, when the movable body 126 is rotated in the coupling direction $C_1$, the position or configuration of the biasing member 154 changes in a manner that increases the potential energy of the biasing member 154. More specifically, the change in the radial position of the member end 226 may cause an increase in the potential energy. The increase in potential energy of the biasing member 154, consequently, causes or increases the rotational force RF of the lift tool 106. The rotational force RF facilitates maintaining the operative engagement between the distal end 108 and the anatomic layer 140. For example, rotational force RF may increase the frictional engagement between the anatomic layer 140 and the projections 132 that pierce the anatomic layer 140.

Notably, at least some level or amount of the rotational force RF is maintained even when the movable body 126 is rotated in limited amounts in the decoupling direction (i.e., in the direction opposite of the coupling direction $C_1$). As shown in FIG. 6, if the movable body 126 is rotated in the decoupling direction about 90° to a third radial position 254, the potential energy of the biasing member 154 in the third radial position 254 is still greater than the potential energy of the biasing member 154 in the first radial position 250. Accordingly, the rotational force RF may still be applied at the distal end 108 even if rotation of the movable body 126 in the decoupling direction occurs.

In some embodiments, the biasing member 154 may also provide a tactile indication to the operator that the operative engagement between the distal end 108 and the anatomic layer 140 still exists. More specifically, when the member end 226 is in the second or third radial positions 252, 254 (or other radial position between the first and second radial positions 250, 252), the operator may sense or detect a rotational force that resists movement in the coupling direction $C_1$. For example, in some cases, if the operator were to release the movable body 126 when the tactile resistance is detected, the biasing member 154 may rotate the movable body 126 in the decoupling direction until the member ends 224, 226 are positioned as shown in FIG. 5. Accordingly, the operator may confirm that the operative engagement exists due to the tactile resistance provided by the biasing member 154.

Figure 7:
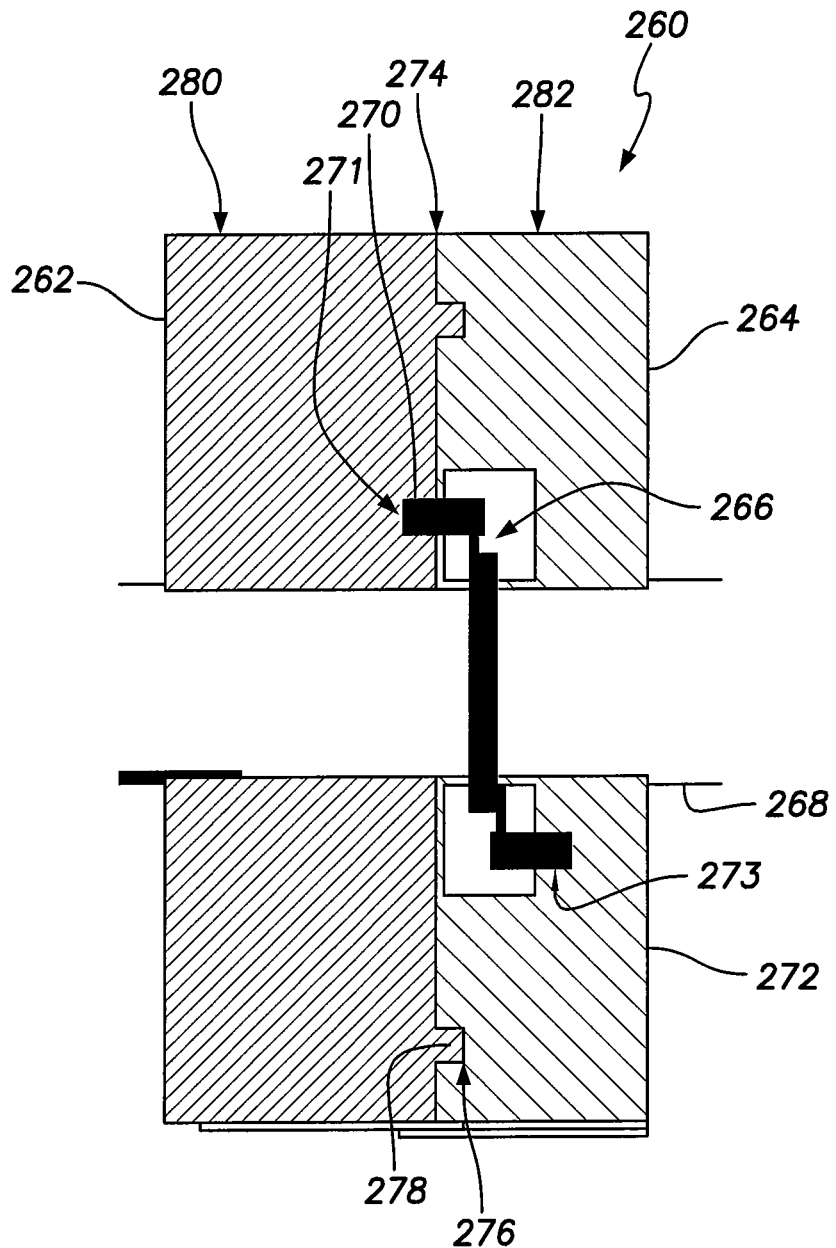
FIG. 7 illustrates a cross-section of a torque applicator formed in accordance with one embodiment that may be used by the medical device of FIG. 1.
Figure 8:
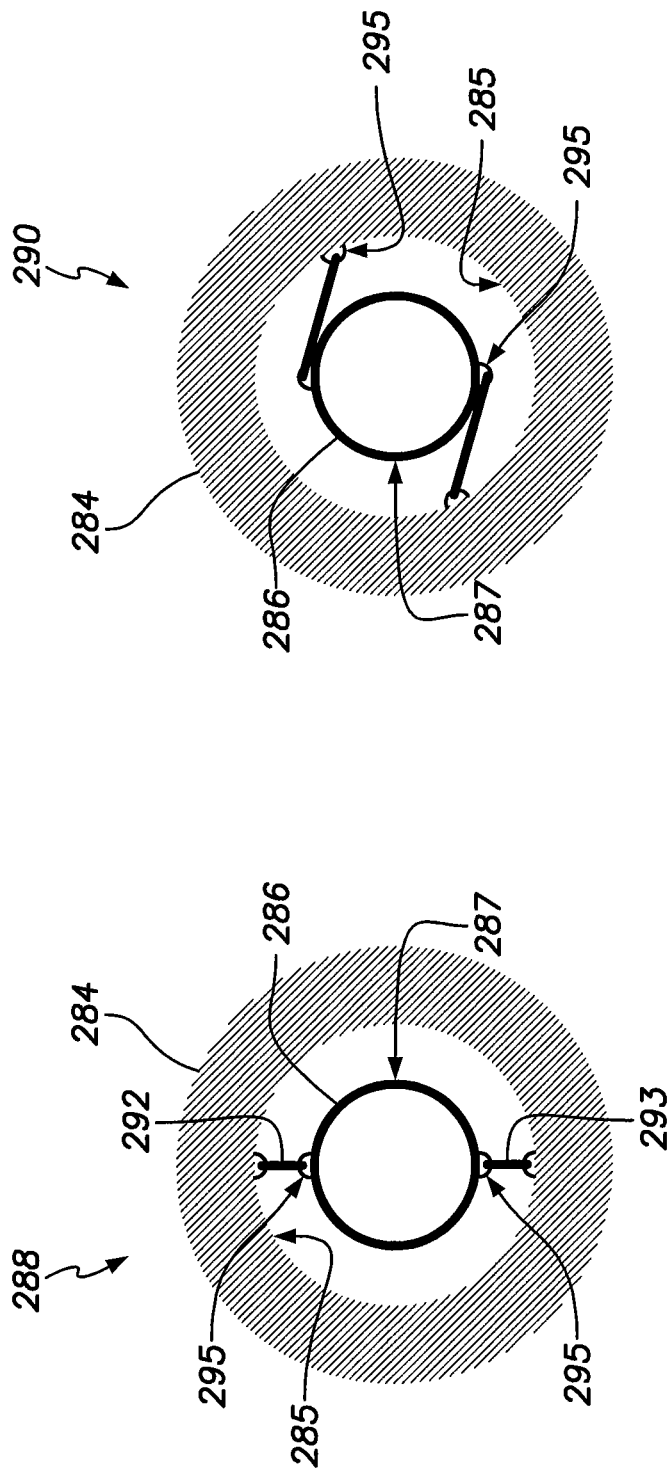
FIG. 8 is an end view of biasing members coupled to a lift tool that may be used by the torque applicator of FIG. 7.

FIGS. 7 and 8 illustrate alternative embodiments of a torque applicator that may be used with the medical device 100 (FIG. 1). The rotational force RF and the tactile resistance may be provided by other torque applicator configurations. For example, FIG. 7 shows a torque applicator 260 that is similarly constructed to the torque applicator 122 (FIG. 1). For example, the torque applicator 260 includes an operator-controlled movable body 262, a shaft or tool holder 264, and a biasing member 266. The biasing member 266 may be similar to or identical to the biasing member 154 (FIG. 3). In the illustrated embodiment, the shaft holder 264 is affixed to a lift tool 268. For example, although not shown, the shaft holder 264 may be affixed to the lift tool 268 using a set screw, plug, or adhesive. The shaft holder 264 and the lift tool 268 may also have complementary projections/recesses for forming a snap-fit engagement. As shown, the biasing member 266 has member ends 270, 272 that are inserted into cavities 271, 273, respectively, of the movable body 262 and the shaft holder 264, respectively.

The movable body 262 and the shaft holder 264 may engage each other along a slidable interface 274. As shown, the shaft holder 264 may have an open-sided channel 276 that receives an annular projection 278 of the movable body 262. In some embodiments, the channel 276 and projection 278 may be configured to limit the rotation of the movable body 262.

In the illustrated embodiment, the movable body 262 is configured to rotate about the lift tool 268. Like the biasing member 154 as described in FIGS. 5 and 6 above, the position or configuration of the biasing member 266 changes in a manner that increases the potential energy of the biasing member 266. Accordingly, the biasing member 266 may provide a rotational force and a tactile indication as described with respect to the torque applicator 122.

In some embodiments, the movable body 262 has an outer surface 280 and the shaft holder 264 has an outer surface 282 in which at least one of the outer surfaces 280, 282 has visible indicators that indicate to the operator that the movable body 262 is applying torque to the lift tool 268. For example, the outer surface 280 may have a series of white lines that are distributed circumferentially around the outer surface 280 in which each line extends along an axial direction. Numbers may be located next to the lines to indicate the number of degrees that the movable body 262 has been rotated. The shaft holder 264 may have a reference line along the outer surface 282 that may be used in conjunction with the lines of the movable body 262.

FIG. 8 shows an isolated end view of an operator-controlled movable body 284 and a lift tool 286 in a first rotational arrangement 288 and in second rotational arrangement 290. The perspective of FIG. 8 is from a loading end (not shown) of the lift tool 286 toward the distal end (not shown). In the first rotational arrangement 288, the movable body 284 has not been rotated about the lift tool 286. In the second rotational arrangement 290, the movable body 284 has been rotated about 60° about the lift tool 286 in a coupling direction (e.g., clockwise).

In the illustrated embodiment, biasing members 292, 293 extend between an inner surface 285 of the movable body 284 and an outer surface 287 of the lift tool 286. The biasing members 292, 293 may be rubber bands or other elastic members that are capable of being stretched and substantially returning to an original shape. The biasing members 292, 293 are attached to respective hooks or clips 295 along the inner and outer surfaces 285, 287. When the movable body 284 is rotated in the coupling direction, the biasing members 292, 293 are stretched longitudinally. As the biasing members 292, 293 are stretched, a potential energy in the biasing members 292, 293 increases. As described above, the potential energy may be translated into a rotational force that facilitates maintaining the operative engagement with the anatomic layer. The potential energy may also provide a tactile resistance to the operator that the lift tool 286 and the anatomic layer are still operatively engaged.

Alternatively or in addition to a torque applicator, embodiments described herein may include a locking mechanism that is configured to hold at least one insert device that extends within a lift tool. Such locking mechanisms may include a locking member that is movable with respect to the insert device. In particular, the locking member may be moved between an engaged position, in which the insert device is in a substantially fixed position, and a released position, in which the insert device is permitted to move axially through the lift tool.

Figure 9:
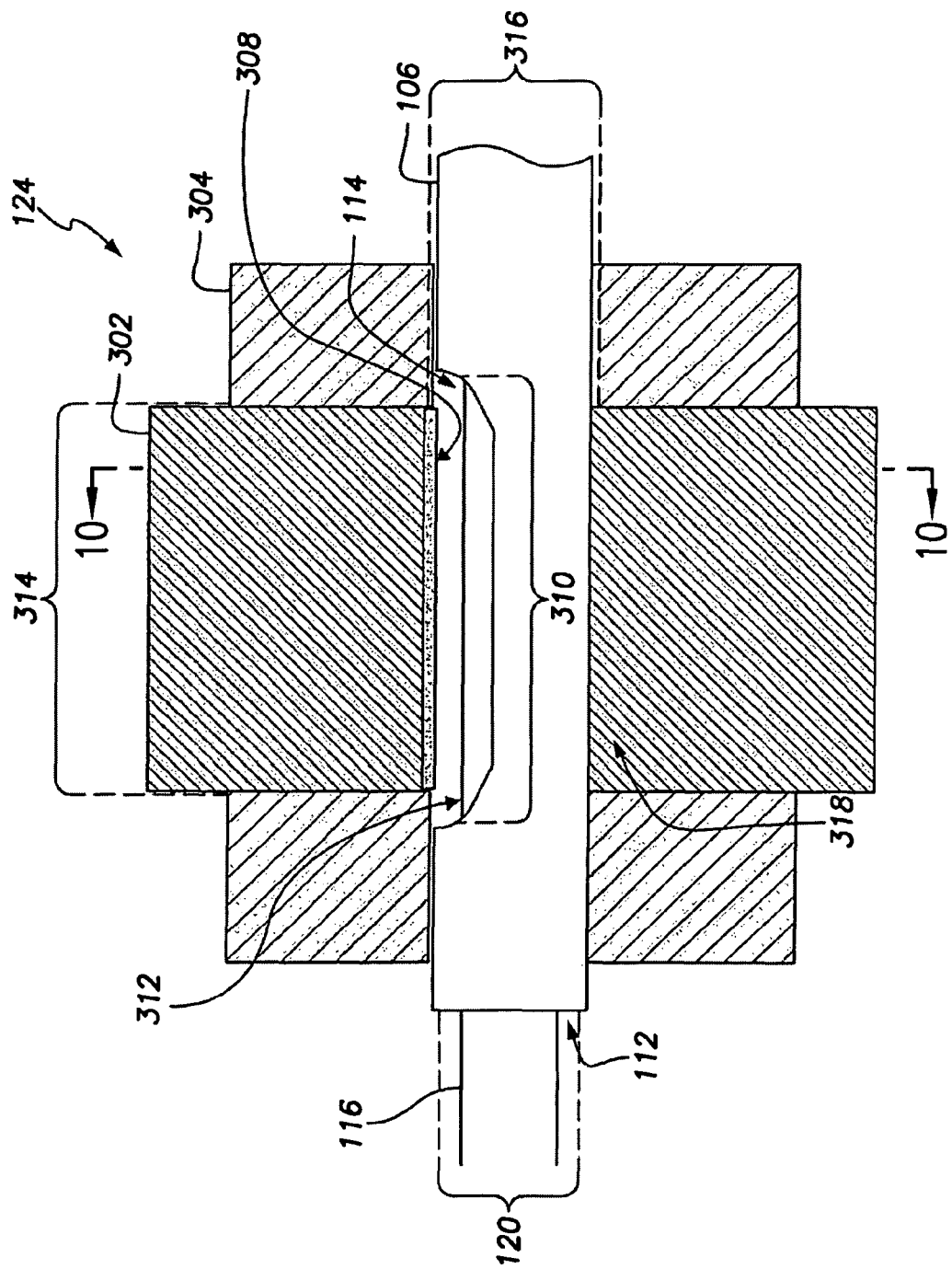
FIG. 9 is a side cross-section of a locking mechanism formed in accordance with one embodiment that may be used with the medical device of FIG. 1.
Figure 10:
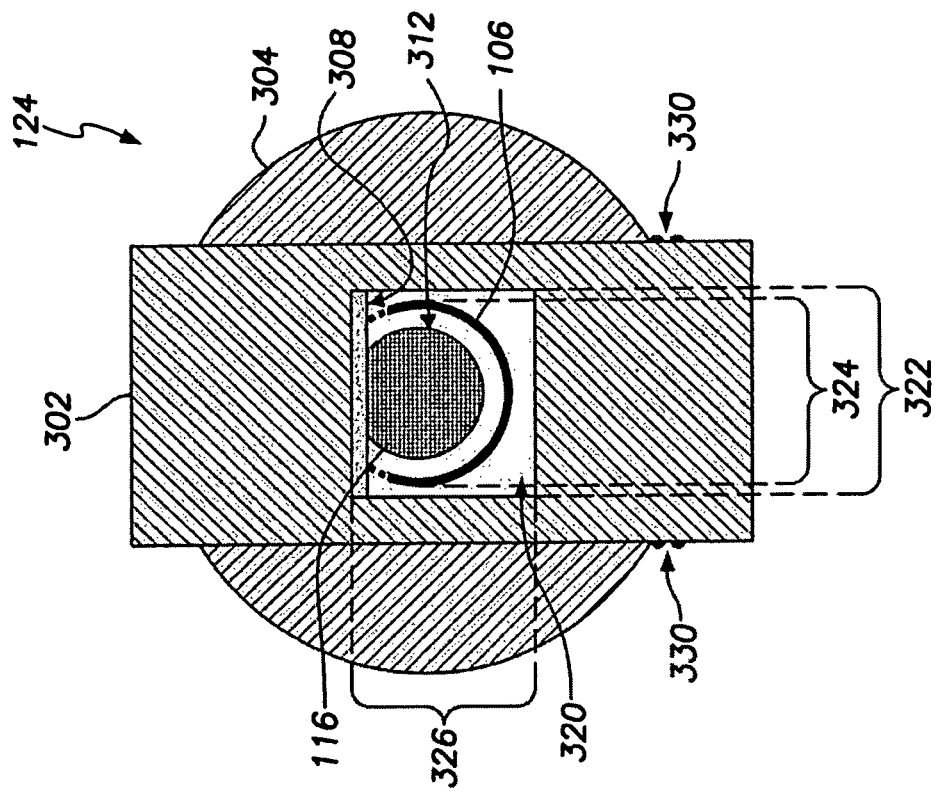
FIG. 10 is an end cross-section of the locking mechanism that may be used with the medical device of FIG. 1.
Figure 11:
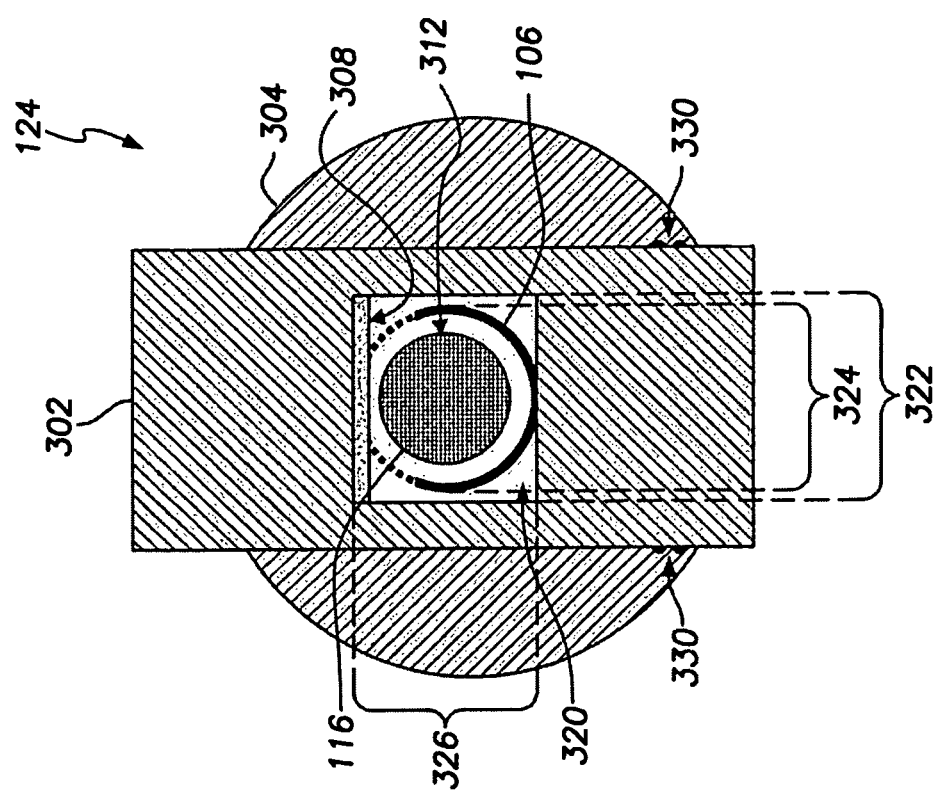
FIG. 11 is an end cross-section of the locking mechanism that may be used with the medical device of FIG. 1.

For example, FIGS. 9-11 illustrate the locking mechanism 124 that is coupled to the lift tool 106 and may be used with the medical device 100 (FIG. 1). More specifically, FIG. 9 is a cross-section of the locking mechanism 124 coupled to the lift tool 106. For illustrative purposes, the lift tool 106 is not shown in a cross-sectional view in FIG. 9. As shown in FIG. 9, the locking mechanism 124 may be coupled proximate to the loading end 112 of the lift tool 106. The loading end 112 includes the opening 120 that is sized and shaped to receive the insert device 116.

In the illustrated embodiment, the locking mechanism 124 includes a locking member 302 and a shaft or tool holder 304 that surrounds the lift tool 106. The shaft holder 304 has a cylindrical shape in FIGS. 9-11 that extends lengthwise along the lift tool 106. However, the shaft holder 304 may have other geometries in alternative embodiments. The shaft holder 304 may directly engage the lift tool 106 and have a fixed position with respect to the lift tool 106. For example, the shaft holder 304 may be directly engaged to the lift tool 106 through hardware (e.g., fasteners) and/or use of an adhesive. The shaft holder 304 is configured to hold the locking member 302 proximate to the lift tool 106. To this end, the shaft holder 304 may include component passages 314, 316 that extend entirely through the shaft holder 304 and intersect each other at a core region 318. The component passage 314 is sized and shaped to receive the locking member 302, and the component passage 316 is sized and shaped to receive the lift tool 106. The component passage 316 extends along the central axis 110 (shown in FIGS. 10 and 11). The component passage 314 extends in a direction that is transverse to the central axis 110.

The insert device 116 is configured to be inserted into and positioned within the shaft lumen 114 of the lift tool 106. As shown, the lift tool 106 includes a lock opening 310. The lock opening 310 is an opening within the lift tool 106 that is located to receive the locking member 302. The lock opening 310 exposes an outer surface 312 of the insert device 116 to an exterior of the lift tool 106. The lock opening 310 is configured to receive an engagement surface 308 of the locking member 302 and permit the engagement surface 308 to directly engage the insert device 116.

FIG. 10 is an end cross-section of the locking mechanism 124 taken along the line 10-10 in FIG. 9 and illustrates the locking mechanism 124 in a released position. FIG. 11 is the end cross-section of the locking mechanism 124 in an engaged position. The locking member 302 is selectively movable with respect to the shaft holder 304 and the insert device 116. As shown, the locking member 302 includes a shaft cavity 320. The shaft cavity 320 may be partially defined by an engagement or interior surface 308 of the locking member 302. The engagement surface 308 is configured to be positioned proximate to (e.g., near or within) the lock opening 310 (FIGS. 9 and 10).

The shaft cavity 320 may be dimensioned to receive the lift tool 106. In particular embodiments, the shaft cavity 320 has a first dimension 322 that is slightly larger than an outer diameter 324 of the lift tool 106, and a second dimension 326 that extends perpendicular to the first dimension 322. In one or more embodiments, the second dimension 326 is sized relative to the lift tool 106 and the insert device 116 within the lift tool 106 so that the locking member 302 is permitted to move relative to the lift tool 106. In some embodiments, the second dimension 326 may be greater than the outer diameter 324. In alternative embodiments, the second dimension 326 is substantially equal to or less than the outer diameter 324.

The locking member 302 may be selectively movable with respect to the insert device 116 between a released position (shown in FIGS. 9 and 10) and an engaged position (shown in FIG. 11). In the released position, the insert device 116 is permitted to move through the shaft lumen 114 along the central axis 110 (FIG. 1). In the engaged position shown in FIG. 11, the locking member 302 engages the insert device 116 and thereby holds the insert device 116 in a fixed position with respect to the locking member 302 and with respect to the lift tool 106. The fixed position may be both a fixed axial position and a fixed rotational position. In such cases, the beveled end 141 (FIG. 1) of the insert device 116 is fixed with respect to the distal end 108 (FIG. 1) in a designated position and orientation.

In some embodiments, the engagement surface 308 is configured to increase friction between the insert device 116 and the engagement surface 308. For example, the engagement surface 308 may include a rubber or elastic-like composition that partially conforms around the insert device 116 and grips the insert device 116.

In some embodiments, the locking member 302 is held within the engaged position so that the operator may let go of the locking mechanism 124 without the locking member 302 returning to released position. The locking member 302 may form an interference fit with the shaft holder 304 or the lift tool 106. By way of example, and with respect to FIGS. 9 and 10, the locking member 302 may include interference members 330 that are configured to engage the shaft holder 304. In the released position, the interference members 330 may impede or resist movement of the locking member 302. In the engaged position, the interference members 330 may resist movement of the locking member 302 back to the released position. In each of the released and engaged positions, the interference members 330 may provide a frictional force that resists movement of the locking member 302. As such, an engagement force may be required from the operator to move the locking member 302 between the release and engaged positions.

Figures 12, 13:
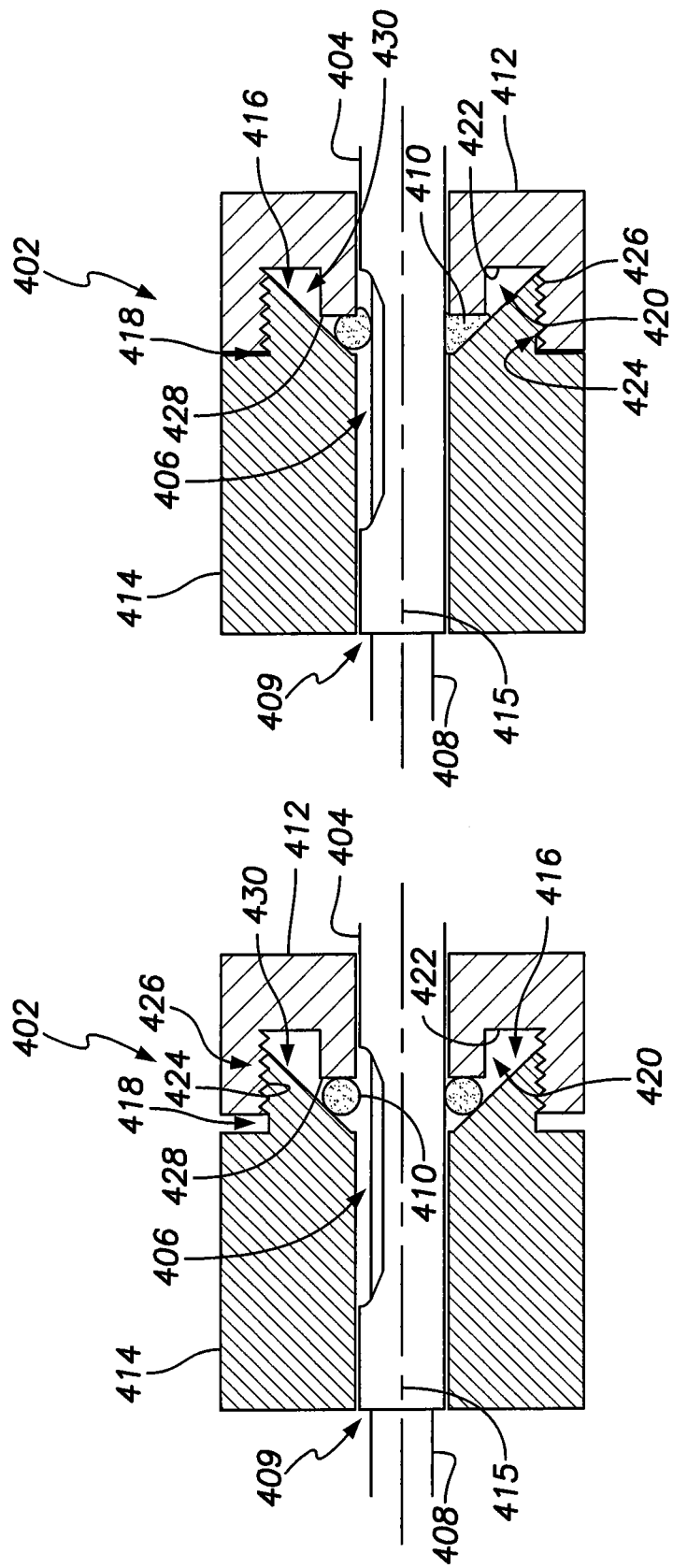
FIG. 12 is a side cross-section of a locking mechanism formed in accordance with one embodiment that may be used with the medical device of FIG. 1.
FIG. 13 is the side cross-section of the locking mechanism of FIG. 12 as the locking mechanism is holding an insert device in a fixed position.

FIGS. 12 and 13 illustrate side cross-sections of a locking mechanism 402 formed in accordance with one embodiment. The locking mechanism 402 is coupled to a lift tool 404 having a shaft lumen 406. The lift tool 404 and the shaft lumen 406 may be aligned with respect to and extend along a central axis 415. The locking mechanism 402 may be positioned proximate to a loading end 409 of the lift tool 404. As shown, the locking mechanism 402 includes a locking member 410, a shaft or tool holder 412, and an operator-controlled movable body 414. In the illustrated embodiment, the locking member 410 is an elastomeric member, such as an O-ring, that surrounds the lift tool 404. The locking member 410 is configured to be moved by the movable body 414 with respect to an insert device 408 when the insert device 408 is located within the shaft lumen 406. For example, FIG. 12 shows the locking member 410 in a released position with respect to the insert device 408, and FIG. 13 shows the locking member 410 in an engaged position with respect to the insert device 408.

The movable body 414 is configured to move bi-directionally along the central axis 415 to engage and disengage the locking member 410. In the illustrated embodiment, the movable body 414 is rotatably engaged with the shaft holder 412. As such, when the movable body 414 is rotated about the lift tool 404 in a first direction (e.g., clockwise), the movable body 414 is driven toward the locking member 410. When the movable body 414 is rotated about the lift tool 404 in a second direction (e.g., counter-clockwise), the movable body 414 is driven away from the locking member 410. However, in alternative embodiments, the movable body 414 may not be rotatable. For example, the movable body 414 may instead be slidable bi-directionally along the lift tool 404.

As shown, the movable body 414 includes a mating end 416 having an outer surface 418. The mating end 416 is disposed within a receiving cavity 420 of the shaft holder 412. More specifically, the shaft holder 412 includes an interior surface 422 that defines the receiving cavity 420 and includes a portion that faces the outer surface 418. In the illustrated embodiment, the outer surface 418 and the interior surface 422 include threads 424, 426, respectively. The threads 424, 426 engage each other and are configured to move the movable body 414 toward (or away) from the shaft holder 412 when the movable body 414 is rotated.

The mating end 416 may include a mating surface 430 that is shaped to at least partially face the insert device 408 and/or the lift tool 404. For example, the mating surface 430 may be shaped conically and surround the central axis 415. In such embodiments, as the movable body 414 is driven toward the shaft holder 412, the mating surface 430 engages the locking member 410. At this time, the locking member 410 may also be pressed against a member-engaging portion 428 of the interior surface 422. As the movable body 414 continues to move toward the shaft holder 412, the locking member 410 is displaced toward the central axis 415 and pressed against the insert device 408. An engagement force at which the locking member 410 is pressed against the insert device 408 may effectively hold the insert device 408 in a fixed position.

As such, the locking mechanism 402 is configured to selectively move the locking member 410 with respect to the insert device 408 between a released position and an engaged position. When the movable body 414 is not engaging the locking member 410, the locking member 410 is in the released position and may be spaced apart from the insert device 408 as shown in FIG. 12. The insert device 408 may be permitted to move axially and rotatably within the shaft lumen 406. In the engaged position, the insert device 116 may have a fixed axial location and a fixed rotational position.

Figure 15:
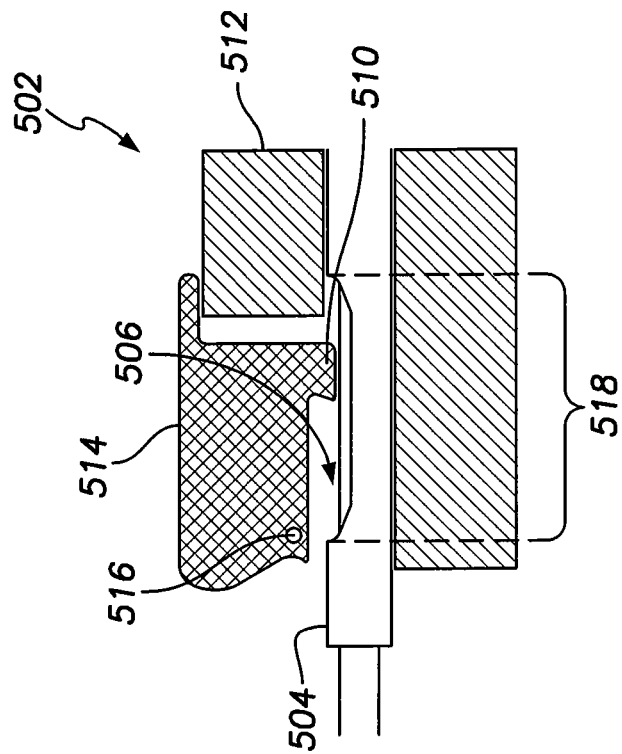
FIG. 15 is the side cross-section of the locking mechanism of FIG. 14 as the locking mechanism is holding an insert device in a fixed position.
Figure 14:
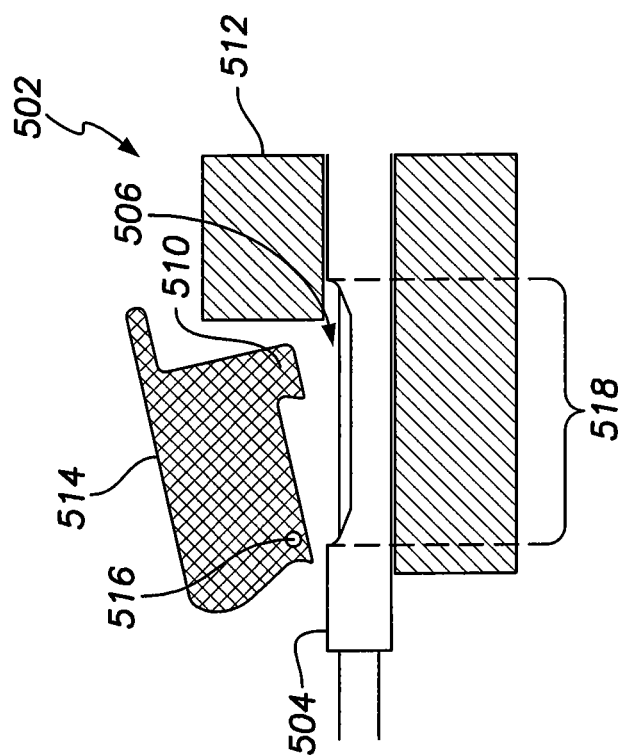
FIG. 14 is a side cross-section of a locking mechanism formed in accordance with one embodiment that may be used with the medical device of FIG. 1.

FIGS. 14 and 15 illustrate side cross-sections of a locking mechanism 502 formed in accordance with one embodiment. The locking mechanism 502 is coupled to a lift tool 504 having a shaft lumen 506. As shown, the locking mechanism 502 includes a locking member 510, a shaft or tool holder 512, and an operator-controlled movable body 514. The shaft holder 512 may be in a fixed position with respect to the lift tool 504 and provide support for the movable body 514. The movable body 514 is configured to be rotated by the operator about an axis of rotation that extends into and out of the page in FIGS. 14 and 15. For example, the movable body 514 may be rotatable about an axle 516 to move the movable body 514 between released and engaged positions.

FIG. 14 shows the locking member 510 in a released position with respect to the insert device 508, and FIG. 15 shows the locking member 510 in an engaged position with respect to the insert device 508. For each of the released and engaged positions, interference members (not shown) may hold the movable body 514 in the respective position such that a force (e.g., from the operator) is required to move the movable body 514 to a different position. In the illustrated embodiment, the locking member 510 is a portion of movable body 514. As such, when the movable body 514 is moved by the operator with respect to the insert device 508, the locking member 510 moves with the movable body 514.

As shown in FIGS. 14 and 15, when the movable body 514 is rotated about the axle 516 from the released position to the engaged position, the locking member 510 is received into the shaft lumen 506 through a lock opening 518 of the lift tool 504 and directly engages the insert device 508 therein. The engagement between the locking member 510 and the insert device 508 may create frictional forces that hold the insert device 508 in a fixed position.

In an alternative embodiment, the locking mechanism 502 may include an O-ring that surrounds the lift tool 504 in a similar manner as the locking member 410 surrounds the lift tool 404 in FIGS. 12 and 13. In this alternative embodiment, the movable body 514 may press into the O-ring and thereby push the O-ring through the lock opening and against the insert device 508.

FIGS. 16 and 17 are images of medical devices 540, 560, respectively, that are each formed in accordance with one embodiment. The medical device 540 includes a lift tool 542, a torque applicator 544, and a locking mechanism 546. The medical device 560 includes a lift tool 562, a torque applicator 564, and a locking mechanism 566. Each of the lift tools 542, 562, the torque applicators 544, 564, and the locking mechanisms 546, 566 may include one or more of the features of the lift tools, torque applicators, and locking mechanisms described herein. For example, the locking mechanisms 546, 566 may be similar or identical to the locking mechanisms 502, 124, respectively. The torque applicators 544, 564 may be similar or identical to the torque applicator 122.

Also shown in FIGS. 16 and 17, the medical devices 540, 560 are holding an insert device 550 that includes a Lure lock 552 and a Tuohy needle 554. The Lure lock 552 is configured to engage an end of the Tuohy needle 554 and facilitate insertion of objects through the Tuohy needle 554. The Luer lock 552 is also shaped to interface with a respective loading end of the lift tool. Also shown, the lift tool 542, 562 have projections 556 (e.g., tines) at the respective distal ends 543, 563. The projections 556 are configured to be embedded into an anatomic layer, such as the parietal pericardium. Object ends 558 of the Tuohy needles 554 are also shown clearing the distal ends 543, 563.

Figure 18:
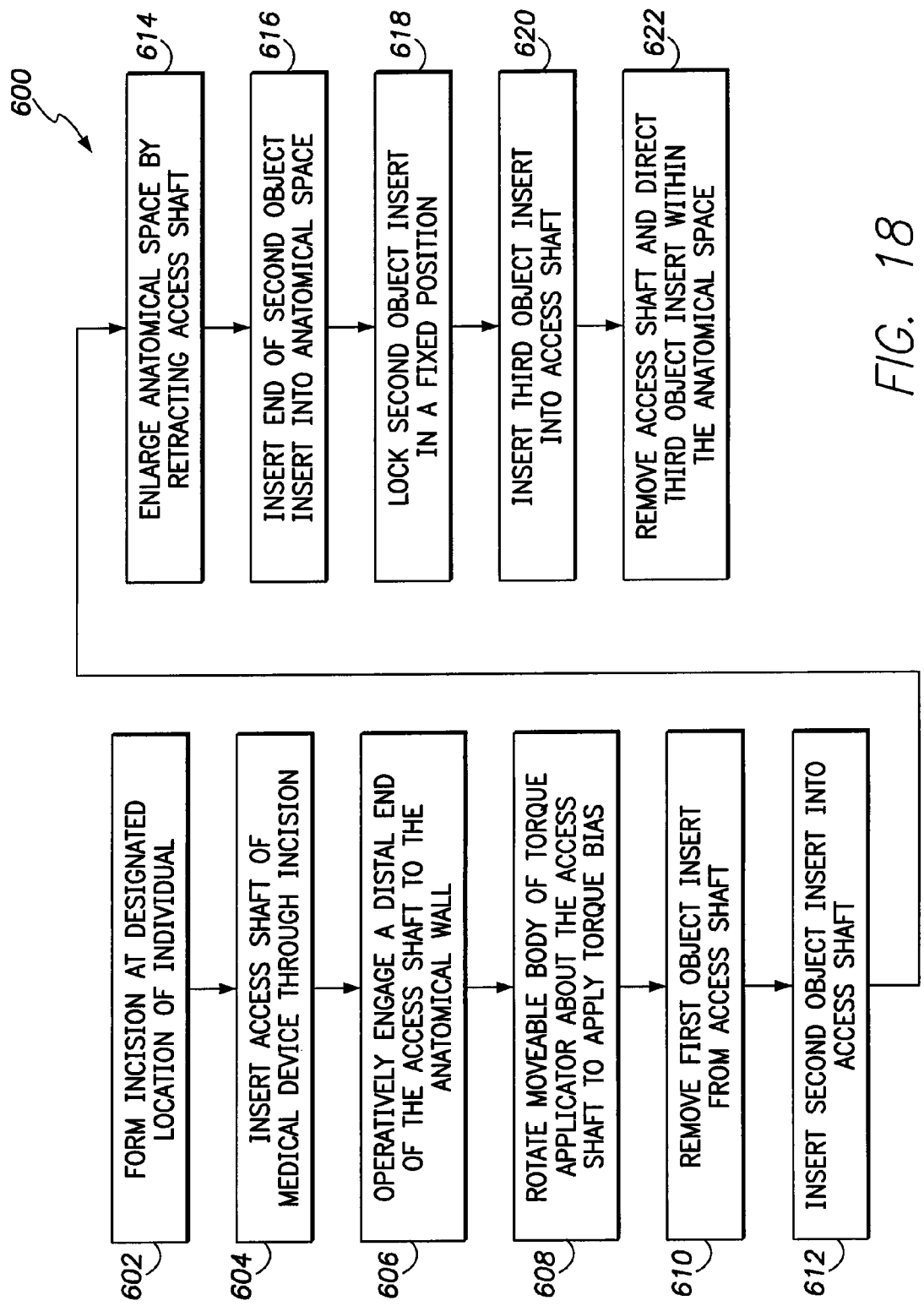
FIG. 18 is a flowchart illustrating a method of accessing an anatomic space in accordance with one embodiment.

FIG. 18 is a flowchart illustrating a method 600 of accessing an anatomic space in accordance with one embodiment. The method 600 is described with specific reference to the anatomic space being the pericardial space that is defined by the parietal pericardium. However, it is understood that the method 600 may be similarly implemented with other anatomical spaces and anatomic layers. The method 600 may include forming, at 602, an incision in the skin of an individual. In certain embodiments in which it is desired to access the pericardial space, the incision may be located just below the xiphoid process. At 604, a lift tool of a medical device may be inserted through the incision. For example, the lift tool may be inserted through the tissues between the subxiphoid wound and the pericardium. In embodiments that include lift tools with projections or tines for gripping tissue, the lift tool may have an obturator that extends beyond the distal end of the lift tool. More specifically, an end of the obturator may clear the distal end of the lift tool and the projections. The obturator may prevent coring in which unwanted fluid or other material flows into the shaft lumen as the lift tool is inserted into the body. Moreover, the obturator may reduce the likelihood of the projections inadvertently snagging tissue.

The lift tool may be inserted until the distal end interfaces with or engages an anatomic layer. By way of example, the operator may insert the lift tool into the body until the operator detects or senses the heart. More specifically, the operator may be able to detect movement of the heart muscle (e.g., contractions) through a handle of the medical device.

At 606, the distal end of the lift tool may be operatively engaged to the anatomic layer. For embodiments that include projections at the distal end, the lift tool may be rotated about a central axis of the lift tool while force is maintained in the insertion direction to embed the projections into the anatomic layer. As described herein, the projections may be shaped (e.g., curved) to pierce and extend into the anatomic layer as the lift tool is rotated. In alternative embodiments, the engagement operation 606 may include generating a vacuum within the shaft lumen to draw a portion (e.g., bleb) of the anatomic layer into the distal end of the lift tool.

One or more of the medical devices used during the method 600 may include a torque applicator and/or a locking mechanism, such as the torque applicators and locking mechanisms described herein.

In certain embodiments, the torque applicator is used after the lift tool has engaged the anatomic layer. For example, the method 600 may include rotating, at 608, a movable body of the torque applicator about the lift tool. The movable body may be operatively coupled to the lift tool through a biasing member. When the movable body is rotated in a coupling direction, a potential energy in the biasing member is increased to thereby provide a rotational force for maintaining the operative engagement. By way of example only, the movable body may be rotated clockwise ¼ to ½ turn to put a slight torque bias on the projections to maintain engagement with the pericardial tissue.

Optionally, the torque applicator may also be used to operatively engage, at 606, the lift tool to the anatomic layer. For example, the biasing member may provide a sufficient rotational force for the projections to pierce the anatomic layer and become embedded in the anatomic layer. In other embodiments, the operations 606, 608 may be caused by separate strokes (e.g., rotations) of the operator or may be caused by the same stroke from the operator. For example, rotating the movable body may cause the lift tool to engage the anatomic layer and may also cause a change in the potential energy of the biasing member.

In some cases, multiple biasing members may be used that have different potential energies. For example, first and second biasing members may be used to provide sufficient force for piercing the anatomic layer. After the distal end is operatively engaged, the first biasing member may be released and the second biasing member may remain. In some cases, the second biasing member may provide a different rotational force than the first biasing member.

Optionally, an insert device may be removed, at 610, from the lift tool. For example, for those embodiments that utilize an obturator as the lift tool is inserted into the body, the obturator may be removed. At 612, a second insert device may be inserted into the shaft lumen. For example, a Tuohy needle may be inserted into the lift tool and advanced toward the anatomic layer. In some embodiments, the Tuohy needle may include an obturator within the lumen of the needle.

Optionally, at 614, the anatomic layer may be drawn away or retracted to enlarge the anatomical space located behind the anatomic layer. In the case of cardiac procedures, retracting the parietal pericardium (e.g., "tenting" the parietal pericardium) enlarges the pericardial space in order to reduce the likelihood of the Tuohy needle puncturing heart tissue behind the parietal pericardium.

At 616, a distal end of the insert device may be inserted through the anatomic layer. For example, the Tuohy needle may be inserted through the lift tool until it is detected at a Luer-lock end that the distal end of the Tuohy is pressing against the pericardial tissue. The distal end of the Tuohy needle may then be inserted through the tented parietal pericardium to access the pericardial space.

After the insert device is inserted through the anatomic layer, the insert device may be locked, at 618, into a fixed position. For example, the method 600 may include utilizing a locking mechanism, such as those described herein, to hold the insert device in a fixed axial location and in a fixed rotational position.

At 620, a third insert device is inserted into the lift tool. For example, a guidewire may be inserted into the Tuohy needle. In some embodiments, the Tuohy needle has an obturator when the Tuohy needle is inserted into the lift tool. Accordingly, prior to the insertion operation at 620, the method may include removing one or more of the insert devices already present in the shaft lumen. More specifically, the method may include removing the obturator of the Tuohy needle.

With the obturator removed, the guidewire may then be inserted into the Tuohy needle, through the distal end of the lift tool, and into the pericardial space. At 622, the medical device may then be removed by sliding the medical device (e.g., the lift tool and any insert device other than the guidewire) along the guidewire. The operator or other qualified individual may then proceed with using the guidewire in the pericardial space.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the elements listed thereafter and equivalents thereof as well as additional elements.

Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings. Also, it is to be understood that phraseology and terminology used herein with reference to device or element orientation (such as, for example, terms like "central," "upper," "lower," "front," "rear," "distal," "proximal," and the like) are only used to simplify description of one or more embodiments described herein, and do not alone indicate or imply that the device or element referred to must have a particular orientation. In addition, terms such as "outer" and "inner" are used herein for purposes of description and are not intended to indicate or imply relative importance or significance.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the presently described subject matter without departing from its scope. While the dimensions, types of materials and coatings described herein are intended to define the parameters of the disclosed subject matter, they are by no means limiting and are exemplary embodiments. Many other embodiments will be apparent to those of skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

Although the inventive subject matter has been described with reference to certain embodiments, persons skilled in the art will recognize that changes may be made in form and detail without departing from the spirit and scope of the invention.

What is claimed is:

1. A medical device comprising:

a lift tool extending along a central axis and having a distal end, the distal end configured to grip an anatomic layer when the lift tool is rotated about the central axis in a coupling direction, the lift tool having a shaft lumen that extends longitudinally through the lift tool and opens at the distal end, the shaft lumen configured to receive an insert device that is movable through the shaft lumen and through the distal end;

a torque applicator coupled to the lift tool, the torque applicator including an operator-controlled movable body and a biasing member, the biasing member operatively coupling the lift tool and the movable body, the biasing member being flexed when the movable body is moved relative to the lift tool to change a potential energy of the biasing member, the potential energy of the biasing member biasing the lift tool in the coupling direction; and the biasing member including a torsion spring having first and second ends, the first end being secured with respect to the lift tool, the second end being secured to the movable body.

2. The medical device of claim 1, wherein the potential energy causes a tactile resistance that is detectable by an operator engaging the movable body.

3. The medical device of claim 1, wherein the movable body is configured to rotate about the central axis.

4. The medical device of claim 3, wherein the biasing member permits the movable body to be rotated about the central axis at least about 90° in a decoupling direction that is opposite the coupling direction while providing a rotational force in the coupling direction.

5. The medical device of claim 1, wherein the torque applicator includes a shaft holder that has a fixed position with respect to the lift tool, the shaft holder securing a portion of the biasing member with respect to the lift tool.

6. The medical device of claim 1, further comprising a locking mechanism coupled to the lift tool, the locking mechanism including a locking member that is selectively movable between a released position and an engaged position with respect to the insert device, the locking member engaging the insert device when in the engaged position to hold the insert device at a fixed position with respect to the lift tool, the locking member permitting the insert device to move through the shaft lumen when in the released position.

7. The medical device of claim 6, wherein the distal end is sized and shaped to operatively engage a parietal pericardium during a medical procedure, the shaft lumen being sized and shaped to receive a hollowed needle, the locking member configured to hold the hollowed needle in a fixed position, wherein the torque applicator is configured to maintain a rotational force to maintain the engagement between the parietal pericardium and the distal end.

8. A medical device comprising:

a lift tool extending along a central axis and having a distal end, the distal end configured to grip an anatomic layer when the lift tool is rotated about the central axis in a coupling direction, the lift tool having a shaft lumen that extends longitudinally through the lift tool and opens at the distal end, the shaft lumen configured to receive an insert device that is movable through the shaft lumen and through the distal end;

a torque applicator coupled to the lift tool, the torque applicator including an operator-controlled movable body and a biasing member, the biasing member operatively coupling the lift tool and the movable body, the biasing member being flexed when the movable body is moved relative to the lift tool to change a potential energy of the biasing member, the potential energy of the biasing member biasing the lift tool in the coupling direction; and the torque applicator including a shaft holder that has a fixed position with respect to the lift tool, the shaft holder securing a portion of the biasing member with respect to the lift tool.

9. The medical device of claim 8, wherein the potential energy causes a tactile resistance that is detectable by an operator engaging the movable body.

10. The medical device of claim 8, wherein the movable body is configured to rotate about the central axis.

11. The medical device of claim 10, wherein the biasing member permits the movable body to be rotated about the central axis at least about 90° in a decoupling direction that is opposite the coupling direction while providing a rotational force in the coupling direction.

12. The medical device of claim 8, further comprising a locking mechanism coupled to the lift tool, the locking mechanism including a locking member that is selectively movable between a released position and an engaged position with respect to the insert device, the locking member engaging the insert device when in the engaged position to hold the insert device at a fixed position with respect to the lift tool, the locking member permitting the insert device to move through the shaft lumen when in the released position.

13. The medical device of claim 12, wherein the distal end is sized and shaped to operatively engage a parietal pericardium during a medical procedure, the shaft lumen being sized and shaped to receive a hollowed needle, the locking member configured to hold the hollowed needle in a fixed position, wherein the torque applicator is configured to maintain a rotational force to maintain the engagement between the parietal pericardium and the distal end.

* * * * *